United States Patent [19]

Tabachnik

[11] Patent Number: 4,837,155

[45] Date of Patent: Jun. 6, 1989

[54] METHOD OF GROWING TRICHODERMA

[75] Inventor: Mordechai Tabachnik, Nes Ziona, Israel

[73] Assignee: Bio-Technology General Corp., New York, N.Y.

[21] Appl. No.: 53,373

[22] Filed: May 22, 1987

Related U.S. Application Data

[63] Continuation of Ser. No. 604,841, Apr. 27, 1984, abandoned.

[30] Foreign Application Priority Data

Apr. 29, 1983 [IL] Israel ......................................... 68523

[51] Int. Cl.$^4$ ................................................ C12N 1/14
[52] U.S. Cl. ..................................... 435/254; 435/171; 435/243; 435/244; 435/248; 435/260; 435/813; 435/818; 435/911; 435/945
[58] Field of Search ................. 435/171, 173, 243-246, 435/248, 249, 254, 260, 813, 818, 911, 945

[56] References Cited

U.S. PATENT DOCUMENTS 4,321,327  3/1982  Chen et al. ........................... 435/161

OTHER PUBLICATIONS

Lewis, J. A. et al., Soil Biology and Biochemistry, vol. 15, No. 3, pp. 351-357, (1983).

Zuker, J. et al., Trans. Br. Mycol. Soc. 76(3): 433-440, (1981).

Annual Review of Microbiology, vol. 35; 459-463, (1981).

*Primary Examiner*—Margaret Moskowitz
*Attorney, Agent, or Firm*—John P. White

[57] ABSTRACT

A method of producing *Trichoderma* conidia in submerged culture comprises first preparing an inoculant of a desired strain of *Tricoderma*. Then, the inoculum is placed in a sufficient volume of a suitable liquid medium. The medium is maintained under substantially constant illumination, agitation and aeration at a temperature from about 25° C. to about 30° C., and a pH from about 5.8 to about 7.0. The culture is grown from a sufficient period of time until the density of conidia is about $5.0 \times 10^8$ per ml, and then the conidia so produced are harvested. A similar method is provided for the production of *Trichoderma* chlamydospores.

31 Claims, No Drawings

METHOD OF GROWING TRICHODERMA

This application is a continuation of U.S. Ser. No. 604,841, filed Apr. 27, 1984, now abandoned.

FIELD OF THE INVENTION

The present invention relates to a method of growing *Trichoderma spp. conidia* and *chlamydospores* in submerged culture particularly on a large scale.

BACKGROUND OF THE INVENTION

Soil-borne pathogenic fungi cause a great deal of damage to seedling crops. These parasites cause damping-off, root-rot, crown-rot, and neck-rot in a wide variety of host plants. The most common pathogenic fungi of this sort are the Rhizoctonia, Pythium, Fusarium, Phytophotora and Sclerotia species. Rhizoctonia, Pythium and Sclerotia species have extraordinarily wide host ranges and are capable of attacking many common commercial crops, such as beans, tomatoes, cotton, peanuts, potatoes, lettuce, flowers and others.

Currently, chemical methods are employed to control these fungi. However, chemicals are potentially hazardous to public health and the environment. They can change the ecosystem and thereby upset the microenvironment of the plants. Furthermore, chemical fungicides are relatively expensive. An alternative to the use of chemicals is the use of biological control agents, which are naturally found in the ecosystem.

Certain species of Trichoderma have been found to possess antagonistic and hyperparasitic properties. A comprehensive review on this is found in Ann Rev. Microbiol. 1981, Vol. 35, pages 459–463. It was thus found that Trichoderma spp. can effectively reduce diseases caused by some soil-borne plant pathogens. The species *T. harzianum, T. hamatum,* and *T. viride* are species of Trichoderma which have been demonstrated to have fungicidal activity against *Sclerotium rolfsii, Rhizoctonia Solani Pythium* spp, and *Fusarium* spp. One serious handicap to commercialization of suitable strains of these fungi for antifungal applications is the lack of a practical large scale production method for these organisms.

The most common method for growing Trichoderma is on solid media which is too expensive and impractical for commercial adaptation. On the other hand, propagation of Trichoderma by a large scale submerged culture process would be most suitable for commercial adaptation, but such a commercial process is not known.

Methods for growing Trichoderma in liquid media, i.e. submerged culture, have been disclosed in the literature. These methods are laboratory processes and do not produce the high yield of spores on a large scale and in a reasonable amount of time as required to make them commercially viable. Elad, Y., et al., (1982) Can. J. Microbiol 28: 719–725; Vezina, C., et al. (1965) Mycologia 57: 722. Thus, for example, Aube and Gagnon, (1969) Can. J. Microbiol, 15:703–705 studied the growth and sporulation of several isolates of *T. viride* in liquid cultures. The method involved growing the organisms for a week in the dark at 20° C. as a stationary culture. Zuber and Turian, (1981) Trans.Br.-Mycol.Soc. 76(3), pg. 433–440 disclose microcycle conidiation of *T. harzianum* in liquid cultures and several growth media are disclosed for this method.

SUMMARY OF THE INVENTION

A method of large scale production of *Trichoderma spp. conidia* in submerged culture which comprises preparing an inoculant of a desired strain of Trichoderma by submerged culture in a suitable liquid culture medium under continuous aeration and placing the inoculant in a sufficient volume of a suitable liquid medium to permit large scale production of *Trichoderma conidia*. The inoculated medium is maintained under substantially constant illumination, agitation and aeration at a temperature from about 25° C. to about 30° C. The pH of the medium is maintained throughout from about 5.8 to about 7.0. The culture is maintained for a sufficient time, until the density of the conidia produced from the inoculant is about $5 \times 10^8$ conidia per ml. The conidia are then harvested.

The medium comprises a carbon source, a nitrogen source, $MgSO_4$, $FeCl_2$, $MnSO_4$, $ZnSO_4$, $KCl$ and $K_2HPO_4$. It can also contain vitamins and antibiotics. The pH is maintained by means of a buffer, preferably a mixture of $K_2HPO_4$ and $KH_2PO_4$.

The carbon source is preferably a combination of potato dextrose broth, with other carbon compounds such as glucose, sucrose, maltose, fructose, cellulose starch, laminarin, malt extract or mixtures thereof. The nitrogen source is preferably ammonium nitrate.

The invention also concerns, a method of large scale production of *Trichoderma spp. chlamydospores* in submerged culture. An inoculant of a desired strain of Trichoderma is prepared in a suitable liquid medium under continuous aeration. The inoculum is placed into a sufficient volume of a suitable liquid culture medium to permit large scale production of *Trichoderma chlamydospores*. The medium contains an amount of a carbon source such that the inoculant forms Trichoderma chlamydospores. The inoculant-containing medium is maintained under substantially constant agitation and aeration at a temperature from about 25° C. to about 30° C. The culture is maintained in the absence of illumination for at least about 24 hours. The *chlamydospores* are then harvested.

The *chlamydospore*-producing medium contains, potato dextrose broth, $KCl$, $K_2HPO_4$, $MgSO_4$, $FeCl_2$, $MnSO_4$, $ZnSO_4$, a vitamin and an antibiotic. It also contains a nitrogen source which is preferably ammonium nitrate.

*Trichoderma spp. conidia* and *chlamydospores* can be produced in large quantities according to these methods and are useful as the active ingredients of fungicidal compositions.

DETAILED DESCRIPTION OF THE INVENTION

The present invention provides a large scale submerged culture method of producing *Trichoderma spp. conidia*.

An inoculant of a desired strain of Trichoderma is first prepared in submerged culture, in a suitable liquid culture medium. The medium is continuously aerated during the growth of the inoculant.

The inoculant so produced is placed into a sufficient volume of a suitable liquid medium to permit large scale production of *Trichoderma spp. conidia*.

The inoculant-containing medium is maintained under substantially constant illumination, agitation and aeration at a temperature from about 25° C. to about 30° C. and at a pH from about 5.8 to about 7.0, for a sufficient period of time until the density of *conidia* produced from the inoculant is a least $5 \times 10^8$ conidia per ml. Once the desired density has been reached the *Trichoderma conidia* so produced are harvested.

To prepare the inoculant any liquid culture medium that is suitable for growing Trichoderma spp. may be used, for example the medium used by Elad et al., (1982), Can J. Microbiol. 28:719-725, and Zuber and Turian, (1981), Trans. Br. Mycol. Soc. 76(3) 433-440. The inoculant can also be cultured in the same medium that will later be used in the large scale production step. The inoculant is grown until a substantial amount of mycelia are obtained, to effectively inoculate a large volume of culture medium. Typically the density of conidia in the inoculum will be about $5 \times 10^8$ *conidia* per ml.

The medium that is suitable for the large scale culture of *Trichoderma spp. conidia* is a liquid basal medium that contains potato dextrose broth as a carbon source. The medium also contains an additional carbon source and a nitrogen source.

In specific embodiments of the invention the carbon source of the medium is a combination of potato dextrose broth with another carbon source selected from the group consisting of glucose, sucrose, maltose, fructose, cellulose, starch and laminarin. The medium may also optionally contain malt extract.

This carbon enriched medium should contain from about 1 to about 4 grams per liter of potato dextrose broth and preferably from about 2 to about 3 grams per liter. It should contain from about 5 to about 15 grams per liter of glucose or its alternatives, e.g., sucrose, maltose, fructose, cellulose, starch laminarin or some other suitable carbon source. Mixtures of these carbon sources can also be used. The concentration of malt extract should be from about 5 to about 15 grams per liter and is preferably from about 8 to about 12 grams per liter. The malt extract is believed to give the conidia more vigor and vitality.

A variety of nitrogen sources can be used, preferably nitrates or nitrites. Ammonium nitrate has been found to be quite suitable for use in this invention.

The medium also contains suitable amounts of minerals and trace elements such as $MgSO_4$, $FeCl_2$, $MnSO_4$, and $ZnSO_4$. Hydrates of these compounds can also be used, e.g. $MgSO_4 \cdot 7H_2O$, $FeCl_2 \cdot H_2O$, $ZnSO_4 \cdot 7H_2O$. The medium also contains suitable amounts $KCl$, and $K_2HPO_4$. Other trace elements and minerals may also be added.

In specific embodiments of the invention the medium contains a vitamin. Thiamine-HCl was found to be suitable as a vitamin, but other vitamins may also be used. The medium may also contain antibacterial compounds such as the antibiotics chloramphenicol, ampicillin, streptomycin or penicillin. Chloramphenicol is the preferred antibacterial compound. It is prefered to use antibiotics that do not have an adverse effect on Trichoderma species.

In a preferred embodiment of the invention the liquid medium comprises per liter of distilled water, $MgSO_4 \cdot 7H_2O$, 0.2 g; KCl, 0.2 g; $K_2HPO_4$, 3.99 g; $KH_2PO_4$, 1.99 g; $FeCl_2 \cdot 4H_2O$, 0.002 g; $MnSO_4 \cdot H_2O$, 0.002 g; $ZnSO_4 \cdot 7H_2O$, 0.002 g; thiamine-HCl, 0.001 g; chloramphenicol, 0.25 g; potato dextrose broth, 2.4 g, glucose, 10.0 g; malt extract, 10.0 g; and $NH_4NO_3$, 1.0 g.

The pH of the culture medium is preferably maintained within a pH range of 5.8 to 7.0, throughout the fermentation process by use of a buffer system. The buffer system used is preferably a phosphate buffer system. In a specific embodiment of this invention the phosphate buffer system used is a mixture of $KH_2PO_4$-$K_2HPO_4$. A Tris-buffer system can also be used.

The inoculant-containing medium can be maintained under constant illumination by using any light source, e.g. incadescent and fluorescent lights can be used. Sunlight can also be used if the reactor vessel containing the medium is sufficiently transparent. The aeration rate for a 50-400 liter volume of culture medium is usually within the range of 0.1-10 vvm.

At the end of the fermentation period the conidia in the medium are harvested. A common way of separating the conidia from the medium is by filtration or centrifugation. After separation the conidia are air dried.

By using the methods of this invention it is possible to grow large quantities of *Trichoderma spp. conidia*. The Trichoderma spp. can be any species of Trichoderma such as *T. harzianum, T. hamatum* or *T. viride*. For example, *T. harzianum* can be grown within 36 to 60 hours to yields of $5 \times 10^8$ to $10^9$ conidia per ml. in 500 liter reactors. The *Trichoderma spp. conidia* grown in large quantities according to this invention can be used as the active ingredient in fungicidal compositions. These fungicidal compositions are useful in protecting commercial plants from soil-borne pathogenic fungi. In a specific embodiment of the invention *Trichoderma harzianum*, T-315, ATCC 20671, *conidia* are grown in large quantities and are used as an active ingredient in fungicidal compositions. In another embodiment of the invention *Trichoderma harzianum* T-35, ATCC 20691, conidia are grown in large quantities and used as an active ingredient in fungicidal compositions.

The invention also concerns a large scale production method for *Trichoderma spp. chlamydospores*.

In this embodiment of the invention an inoculant of a desired strain of Trichoderma spp. is prepared in submerged culture. A suitable liquid culture medium is used, as described previously, and the medium is continuously aerated during the growth of the inoculant.

The inoculant so produced is placed into a sufficient volume of a suitable liquid medium to permit large scale production of *Trichoderma spp. chlamydospores*. This medium is a carbon limited medium which contains an amount of a carbon source such that the inoculant forms *Trichoderma spp. chlamydospores*.

The inoculant containing medium is maintained under substantially constant agitation and aeration at a temperature from about 25° C. to about 30° C. in the absence of illumination for at least about 24 hours. The pH of the medium is not maintained. The *Trichoderma chlamydospores* so produced are then harvested.

The carbon limited medium used for the production of *chlamydospores* comprises about 1 to about 3 grams per liter of potato dextrose broth. The nitrogen source in the medium may be a nitrate or nitrite but is preferably ammonium nitrate.

The medium also contains suitable amounts of minerals and trace elements such as $MgSO_4$, $FeCl_2$, $MnSO_4$, and $ZnSO_4$. Hydrates of these compounds can also be used e.g. $MgSO_4 \cdot 7H_2O$, $FeCl_2 \cdot 4H_2O$, $MnSO_4 \cdot H_2O$, $ZnSO_4 \cdot 7H_2O$. The medium also contains suitable amounts of $KCl$, and $K_2HPO_4$. Other trace elements and minerals may also be added.

In specific embodiments of the invention the basal medium also contains a vitamin. Thiamine-HC1 was found to be a suitable vitamin but other vitamins may also be used. The basal medium may also contain antibacterial compounds such as the antibiotics chloramphenicol, ampicillin, streptomycin and penicillin. Chloramphenicol is the preferred antibiotic compound. It is prefered that an antibiotic be used which does not have an adverse effect on Trichoderma, spp.

In a preferred embodiment of the invention the culture medium for *chlamydospores* comprises, in grams per liter of distilled water, KCl, 0.2 g; $K_2HPO_4$, 0.9 g; $FeCl_2 \cdot 4H_2O$, 0.002 g; $MnSO_4 \cdot H_2O$, 0.002 g; $ZnSO_4 \cdot 7H_2O$, 0.002 g; thiamine-HCl, 0.001 g; chloramphenicol, 0.25 g; $MgSO_4 \cdot 7H_2O$, 0.2 g; $NH_4NO_3$, 1.0 g; and from about 1.2 to about 2.4 g of potato dextrose broth.

The inoculant may be grown in the same medium that is used for the large scale culture of *chlamydospores*. In a specific embodiment of the invention *Trichoderma spp. conidia* grown in accordance with the methods of this invention can be used as an inoculant for the production of chlamydospores. These *conidia* can be grown either on a small or large scale before being used as the inoculant.

In a preferred embodiment of this invention *Trichoderma spp. conidia* are first grown on a large scale in submerged culture according to the methods of this invention. The *conidia* so produced are placed into a sufficient volume of a suitable liquid medium to permit the large scale production of *Trichoderma chlamydospores*. The chlamydospore medium contains an amount of a carbon source such that the conidia form *chamydospores* and is described above.

The Trichoderma-containing medium is maintained under substantially constant agitation and aeration at a temperature from about 25° C. to about 30° C. in the absence of illumination for at least about 24 hours. The pH of this medium is not maintained. In accordance with this invention mycelia highly enriched in *chlamydospores* are obtained. The *chlamydospores* are harvested by first breaking the mycelia, e.g. with ultrasonic waves. The *chlamydospores* may then be separated by filtration or centrifugation.

In accordance with this invention large quantities of *Trichoderma spp chlamydospores* can be produced. The Trichoderma spp. can be any species such as *T.harzianum, T.hamatum* or *T.viride*. *Chlamydospores* grown according to this invention are useful in fungicidal compositions.

In a specific embodiment of the invention large quantities of *T.harzianum*, T-315, ATCC 20671, *chlamydospores* are produced and used as an active ingredient in fungicidal compositions. In another embodiment of the invention *T.harzianum* T-35, ATCC 20691, *chlamydospores* are produced in large quantities and used as an active ingredient in fungicidal compositions. Such fungicidal compositions are useful in protecting commercial crops from soil-borne pathogens.

EXAMPLE 1

*Conidia* was harvested from a biologically pure culture of *T.harzianum*, T-315, ATCC 20671, and inoculated on a carbon enriched liquid medium in baffled Erlenmeyer flasks. The liquid medium was a sterile medium comprising (g/l distilled water):

| Potato Dextrose Broth | 2.4 | $KH_2PO_4$ | 1.99 |
| Glucose | 10.0 | $FeCl_2.4H_2O$ | 0.002 |
| Malt Extract | 10.0 | $MnSO_4.H_2O$ | 0.002 |
| $NH_4NO_3$ | 1.0 | $ZnSO_4.7H_2O$ | 0.002 |
| $MgSO_4.7H_2O$ | 0.2 | Thiamine-HCl | 0.001 |

-continued

| KCl | 0.2 | Cloramphenicol | 0.25 |
| $K_2HPO_4$ | 3.99 | | |

The flasks were vigorously aerated on a rotary shaker at 200 rpm at the temperature of 28° C. After 24 to 48 hours, the mycelia produced was homogenized in an Ultra Turrax homogenizer (Janke & Kunkel, Ika Werk) and collected to form a 1 liter initial inoculum.

The homogenized inoculum was inoculated on 50 liters of the same liquid medium in a fermentor. During the following 48 to 65 hour growth period, the pH of the medium was kept between 5.8 and 7.0, and the temperature was maintained at 28°–29° C. A Silicone "Sigma" Antifoam A or C emulsion was added by means of a peristaltic pump controlled by a foam sensing probe. The aeration rate was 5 liters per minute. The culture was continuously illuminated by means of a fluorescent light throughout the 48 to 65 hour growth and *conidial* production period.

Growth was stopped after 48 to 65 hours when the conidial yield density of about $5 \times 10^8$ conidia/ml was reached.

By increasing the aeration rate it is possible to shorten the growth time to 36–48 hours.

What is claimed is:

1. A method for the production of *Trichoderma harzianum* or *Trichoderma hamatum* conidia in submerged culture comprising:
   (a) preparing an inoculant of *Trichoderma harzianum* or *Trichoderma harzianum* or *Trichoderma hamatum* in submerged culture in a suitable liquid culture medium, the medium being continuously aerated at a rate of 0.1 to 10.0 vvm during growth of the inoculant;
   (b) placing the inoculant into a fermentor containing at least 50 liters of a suitable carbon enriched liquid medium permitting production of *Trichoderma conidia;*
   (c) maintaining the inoculant-containing, carbon enriched, liquid medium under substantially constant illumination, agitation and aeration at a temperature from about 25° C. to about 30° C. and at a buffered pH from about 5.8 to about 7.0 for at least 36 hours until the density of *conidia* produced from the inoculant is at least $5 \times 10^8$ conidia per ml.; and
   (d) harvesting the *Trichoderma conidia* so produced.

2. A method in accordance with claim 1, wherein the medium in step a is the same as the medium in step b.

3. A method in accordance with claim 1, wherein the medium in step b includes as a carbon source a combination of potato dextrose broth and a second carbon source selected from the group consisting of glucose, sucrose, maltose, fructose, cellulose, starch, laminarin, or mixtures thereof.

4. A method in accordance with claim 3, wherein the medium also contains malt extract.

5. A method in accordance with claim 4, wherein the second source is glucose.

6. A method in accordance with claim 3, wherein the concentration of potato dextrose broth is about 1 to about 4 grams per liter.

7. A method in accordance with claim 3, wherein the concentration of the second carbon source is about 5 to about 15 grams per liter.

8. A method in accordance with claim 4, wherein the concentration of malt extract is about 5 to about 15 grams per liter.

9. A method in accordance with claim 1, wherein the medium includes ammonium nitrate as a nitrogen source.

10. A method in accordance with claim 1, wherein the buffer is a mixture of $KH_2PO_4$ and $K_2HPO_4$.

11. A method in accordance with claim 1, wherein the medium includes suitable amounts of $MgSO_4$, $FeCl_2$, $MnSO_4$, $ZnSO_4$, KCl and $K_2HPO_4$.

12. A method in accordance with claim 11, wherein the medium also contains an antibiotic which does not adversely effect *Trichoderma harzianum* or *Trichoderma hamatum*.

13. A method in accordance with claim 11, wherein the medium also contains a vitamin.

14. A method is accordance with claim 13, wherein the vitamin is thiamine-HCl.

15. A method in accordance with claim 12, wherein the antibiotic is chloramphenicol.

16. A method in accordance with claim 5, wherein the medium comprises per liter of distilled water, $MgSO_4 \cdot 7H_2O$ 0.2 g; KCl, 0.2 g; $K_2HPO_4$, 3.99 g; $KH_2PO_4$, 1.99 g; $FeCl_2 \cdot 4H_2O$, 0.002 g; $MnSO_4 \cdot H_2O$, 0.002 g; $ZnSO_4 \cdot 7H_2O$, 0.002 g; thiamine-HCl, 0.001 g; chloramphenicol, 0.25 g; potato dextrose broth, 2.4 g; glucose, 10.0 g; malt extract, 10.0 g; and $NH_4NO_3$ 1.0 g.

17. A method in accordance with claim 1, wherein the Trichoderma spp. is *T.harzianum*, T-315, ATCC 20671.

18. A method in accordance with claim 1 wherein the Trichoderma spp. is *T.harzianum*, T-35, ATCC 20691.

19. A method for the production of *Trichoderma harzianum* or *Trichoderma hamatum* chlamydospores in submerged culture comprising:
   (a) preparing an inoculant of *Trichoderma harzianum* or *Trichoderma hamatum* in submerged culture in a suitable liquid culture medium, the medium being continously aerated during growth of the inoculant;
   (b) placing the inoculant into a fermentor containing at least 50 liters of a suitable carbon limited liquid medium permitting production of *Trichoderma chlaymdospores;*
   (c) maintaining the inoculant-containing, carbon limited liquid medium under substantially constant agitation and aeration at a temperature from about 25° C. to about 30° C., in the absence of illumination and without maintaining the pH of the medium, for at least about 24 hours; and
   (d) harvesting the *Trichoderma chlamydospores* so produced.

20. A method in accordance with claim 19, wherein the medium in step (a) is the same as the medium in step (b).

21. A method in accordance with claim 19, wherein the medium in step (b) includes as a carbon source about 1 to about 3 grams per liter of potato dextrose broth.

22. A method in accordance with claim 19, wherein the medium includes ammonium nitrate as a nitrogen source.

23. A method in accordance with claim 19, wherein the medium includes suitable amounts of $MgSO_4$, $FeCl_2$, $MnSO_4$, $ZnSO_4$, KCl and $K_2HPO_4$.

24. A method in accordance with claim 23, wherein the medium also contains a vitamin.

25. A method in accordance with claim 24, wherein the vitamin is thiamine-HCl.

26. A method in accordance with claim 19, wherein the medium comprises per liter of distilled water, about 1.2 g to about 2.4 g. potato dextrose broth, KCl 0.2 g; $K_2HPO_4$, 0.9 g; $FeCl_2 \cdot 4H_2O$, 0.002 g; $MnSO_4 \cdot H_2O$, 0.002 g; $ZnSO_4 \cdot 7H_2O$, 0.002 g; thiamine-HCL 0.001 g; chloramphenicol 0.25 g; $MgSO_4 \cdot 7H_2O$, 0.2 g; and $NH_4NO_3$, 1.0 g.

27. A method in accordance with claim 19, wherein the Trichoderma spp. is *T.harzianum*, T-315, ATCC 20671.

28. A method in accordance with claim 19, wherein the Trichoderma spp. is *T.harzianum*, T-35, ATCC 20691.

29. A method in accordance with claim 25, wherein the medium also contains an antibiotic which does not adversely effect *Trichoderma harzianum* or *Trichoderma hamatum*.

30. A method in accordance with claim 29, wherein the antibiotic is chloramphenicol.

31. A method for the production of *Trichoderma harzianum* or *Trichoderma hamatum* chlamydospores in submerged culture comprising:
   (a) preparing *Trichoderma harzianum* or *Trichoderma hamatum* conidia according to the method of claim 1;
   (b) placing the *Trichoderma conidia* so prepared into a fermentor containing at least 50 liters of a suitable, carbon limited liquid medium permitting production of *Trichoderma chlamydospores;*
   (c) maintaining the Trichoderma-containing, carbon limited liquid medium under substantially constant agitation and aeration at a temperature from about 25° C. to about 30° C., in the absence of illumination and without maintaining the pH of the medium, for at least about 24 hours; and
   (d) harvesting the *Trichoderma chlamydospores* so produced.

* * * * *